(12) United States Patent
Johnson et al.

(10) Patent No.: US 12,262,900 B2
(45) Date of Patent: Apr. 1, 2025

(54) BONE HOOK PLATE APPARATUS, SYSTEM, AND METHOD

(71) Applicant: Vilex in Tennessee, Inc., McMinnville, TN (US)

(72) Inventors: Brock Johnson, McMinnville, TN (US); Daniel J. Triplett, Smithfield, UT (US)

(73) Assignee: Vilex LLC, Park City, UT (US)

( * ) Notice: Subject to any disclaimer, the term of this patent is extended or adjusted under 35 U.S.C. 154(b) by 41 days.

(21) Appl. No.: 17/858,173

(22) Filed: Jul. 6, 2022

(65) Prior Publication Data

US 2024/0008882 A1    Jan. 11, 2024

(51) Int. Cl.
| | | |
|---|---|---|
| A61B 17/17 | (2006.01) | |
| A61B 17/064 | (2006.01) | |
| A61B 17/56 | (2006.01) | |
| A61B 17/80 | (2006.01) | |
| A61B 17/88 | (2006.01) | |

(52) U.S. Cl.
CPC ...... *A61B 17/1728* (2013.01); *A61B 17/8057* (2013.01); *A61B 17/808* (2013.01); *A61B 17/0642* (2013.01); *A61B 17/1739* (2013.01); *A61B 2017/564* (2013.01); *A61B 17/8004* (2013.01); *A61B 17/8061* (2013.01); *A61B 17/809* (2013.01); *A61B 17/8897* (2013.01)

(58) Field of Classification Search
CPC . A61B 17/8061; A61B 17/808; A61B 17/809; A61B 17/92; A61B 17/1728; A61B 17/1739; A61B 17/1775; A61B 17/8057; A61B 17/846; A61B 17/0642; A61B 17/80; A61B 17/8004; A61B 17/8019; A61B 17/8872; A61B 2017/922; A61B 2017/564; A61B 2017/0645; A61F 2/46; A61F 2/4611; A61F 2/4603; A61F 2002/4622; A61F 2002/4625
USPC ....... 606/96, 280, 281, 286, 291, 297, 86 R, 606/86 B, 915, 99, 279
See application file for complete search history.

(56) References Cited

U.S. PATENT DOCUMENTS

| | | |
|---|---|---|
| 3,824,995 A | 7/1974 | Getscher et al. |
| 5,674,222 A | 10/1997 | Berger et al. |
| (Continued) | | |

FOREIGN PATENT DOCUMENTS

| | | |
|---|---|---|
| CN | 203736290 U | 7/2014 |
| CN | 104783876 A | 7/2015 |
| (Continued) | | |

OTHER PUBLICATIONS

In2bones, 5MS Pseudo Jones Hook Plate https://i2b-usa.com/5ms-pseudo-jones-hook-plate/ accessed Mar. 2022.

(Continued)

*Primary Examiner* — Marcela I. Shirsat
(74) *Attorney, Agent, or Firm* — David Meibos; Maywood IP Law

(57) ABSTRACT

A bone implant, system, and method for retaining a bone fragment. The implant includes at least one hook that includes a base extending proximal to a proximal end of the implant, a bend, and a prong that extends from the bend. The prong slidably engages a guide feature that guides the at least one hook into a corresponding opening in the bone fragment.

34 Claims, 9 Drawing Sheets

(56) References Cited

U.S. PATENT DOCUMENTS

| | | | |
|---|---|---|---|
| 6,379,359 B1 | 4/2002 | Dahners | |
| 7,578,825 B2 | 8/2009 | Huebner | |
| 8,998,969 B2 | 4/2015 | Deffenbaugh et al. | |
| 9,283,010 B2 | 3/2016 | Medoff et al. | |
| 9,636,157 B2 | 5/2017 | Medoff | |
| 9,707,022 B2 | 7/2017 | Huebner et al. | |
| 10,039,579 B2 | 8/2018 | Medoff et al. | |
| 10,231,762 B2 | 9/2019 | Steinhauer et al. | |
| 2003/0040748 A1* | 2/2003 | Aikins | A61B 17/92 606/70 |
| 2006/0004361 A1* | 1/2006 | Hayeck | A61B 17/809 606/291 |
| 2009/0275991 A1* | 11/2009 | Medoff | A61B 17/8061 606/297 |
| 2010/0234896 A1* | 9/2010 | Lorenz | A61B 17/842 606/286 |
| 2013/0046314 A1 | 2/2013 | Medoff et al. | |
| 2013/0046349 A1* | 2/2013 | Medoff | A61B 17/809 606/297 |
| 2014/0039561 A1 | 2/2014 | Weiner et al. | |
| 2014/0135849 A9 | 5/2014 | Medoff | |
| 2015/0134011 A1* | 5/2015 | Medoff | A61B 17/8061 606/286 |
| 2020/0100820 A1* | 4/2020 | Hollis | A61B 17/0401 |
| 2020/0261101 A1 | 8/2020 | Medoff | |
| 2022/0061898 A1 | 3/2022 | Gault et al. | |

FOREIGN PATENT DOCUMENTS

| | | |
|---|---|---|
| CN | 111467015 A | 7/2020 |
| EP | 2702955 A1 | 3/2014 |
| KR | 101794478 B1 | 12/2017 |

OTHER PUBLICATIONS

TriMed, Fifth Metatarsal Hook Place Surgical Technique (2020) https://trimedortho.com/wp-content/uploads/2018/05/LC-72-9000-00S-REV-C-STM-5th-MetaHookPlate.pdf.

Synthes, 3.5 mm LCP Hook Plate. Part of the Synthes locking compression plate (LCP) system, http://synthes.vo.llnwd.net/o16/Mobile/Synthes%20North%20America/Product%20Support%20Materials/Technique%20Guides/SUSA/SUTG3.5LCPhookpltJ8742B.pdf Accessed on May 24, 2022.

TriMed, Ankle Hook Plate Surgical Technique (2022) https://trimedortho.com/wp-content/uploads/2021/09/LC-72-8000-002-REV-2.0-STM-AnkleHookPlate_Web.pdf.

* cited by examiner

BONE HOOK PLATE APPARATUS, SYSTEM, AND METHOD

TECHNICAL FIELD

The present disclosure relates to surgical systems, methods, instruments, and/or devices. More specifically, the present disclosure relates to improved surgical systems, methods, devices, and/or instruments for engaging end bone fragments of a patient's body.

BACKGROUND

Bone fractures on an end a patient's bone can be challenging to properly reduce and fixate. On reason for this is that the bone fragment that separates from the bone (referred to as the parent bone) may be relatively small and therefore provide a minimal amount of bone to engage with an implant and/or a fastener. Furthermore, adequate compression of a reduced fracture proximal to an end of a patient's bone can be challenging if the end of the bone connects to one or more ligaments or tendons that pull the bone fragment away from the parent bone. In certain patients, the fracture may be an avulsion fracture proximal to an end of the bone.

Hook bone plates (a bone plate having one or more prongs or hooks on one end) have been introduced to address these challenges. Hook plates seek to secure a reduced fracture proximal to a bone end and to provide compression to encourage healing of the fracture. However, conventional hook bone plates have limitations. First, the locations of bone ends that are not articular surfaces may be in areas where a patient's skin has less soft tissue, less cushioning tissue (e.g., fatty tissue) between the bone and the skin surface. Consequently, despite a surgeon's best efforts, conventional hook plates can stand proud of the bone surface causing discomfort and/or irritation for the patient.

To overcome these challenges a surgeon may try different options, such as drilling pilot holes for one or more hooks of a hook plate into the bone fragment, tamping the bone hook plate to drive the hooks through the cortical layer of the bone fragment, and the like. Drilling pilot holes can result in difficulty for the surgeon locating the pilot holes beneath the peritoneum when deploying the hook plate. Tamping a hook plate to drive hooks into the bone fragment can be difficult because of the high tamping force required to overcome the strength of the cortical bone of the bone fragment, the size of the bone fragment, and/or the dislocation of a reduction of the fracture caused by the tamping. These efforts have been largely unsuccessful, so much so that surgeons may not consider conventional hook plates as a treatment option.

Accordingly, a need exists for an improved hook that is contoured to a surface of the bone, securely engages a bone fragment, compresses the reduced fracture, and can be readily deployed.

SUMMARY

The various apparatus, devices, systems, and/or methods of the present disclosure have been developed in response to the present state of the art, and in particular, in response to the problems and needs in the art that have not yet been fully solved by currently available technology. One general aspect of the present disclosure can include an implant configured to retain a bone of a patient. The implant includes a body extending between a proximal end and a distal end; and a hook that may include: a base extending proximal to the proximal end and a bend. The implant includes a prong extending from the bend, the prong slidably engages a guide feature configured to guide the hook into an opening in the bone.

Implementations may include one or more of the following features. An implementation of the implant where the prong may include an alignment feature configured to slidably engage the guide feature. The alignment feature may include a cannula which may include: a first opening near the prong; a second opening opposite the first opening, the second opening proximal to the bend; and a first diameter greater than a second diameter of the guide feature.

The alignment feature may also include: a groove that extends along at least a portion of the hook, the groove may include a contact surface that engages the guide feature as the guide feature guides the hook into the opening in the bone; and where the contact surface may include a contour shape selected from the group may include of a curve shape and an open polygon shape. The alignment feature may include at least one rail that extends from the hook, the rail may include a contact surface that slides along the guide feature as the guide feature guides the hook into the opening in the bone. The hook may extend from the proximal end and wrap around at least a portion of an end of the bone; and the alignment feature may be proximal to the prong of the hook. The alignment feature slides linearly along the guide feature and seats wholly within the opening in the bone. The second hook may include a second alignment feature configured to engage a second guide feature to guide the second hook into a second opening in the bone. The hook and second hook can define an open space between them sized to accept a bone fastener inserted into the bone, the bone fastener may include a head having a diameter greater than the open space. The guide feature guides the hook into the opening of the bone such that the bend contacts the bone proximal to the opening in the bone.

One general aspect of the present disclosure can include a placement guide which may include: a placement guide body; a bone plate template that extends from the placement guide body, the bone plate template may include a fastener template configured to identity a location for a fastener of a hook plate; two insertion guides that orient two guide wires as the guide wires are inserted into and engage a bone fragment. The system includes an inserter may include: a coupler configured to releasably engage a hook plate, and an inserter body that extends proximally from a hook plate engaged by the coupler.

Implementations may include one or more of the following features. A hook plate system where the bone plate template of the placement guide may include an inferior surface configured to match at least a portion of an inferior surface of a hook plate. The fastener template may include a stop configured to interfere with insertion of a fastener into the fastener template. The placement guide may include at least a portion of an inferior surface configured to sit proximal to a distal end of the bone fragment without interference from one or more hooks of a hook plate. The insertion guides may include openings that extend from one side of the placement guide body to an opposite side and the openings are parallel to each other. The placement guide may include an engagement feature proximal to the insertion guides, the engagement feature can be configured to engage a surface of the bone fragment. Each of the cannulated hooks may include a cannula configured to slide along one of the guide wires and at least partially into an opening in at least the bone fragment, the opening circumscribing the one of the guide wires.

One general aspect of the present disclosure can include a method for deploying a hook plate in a bone fragment at an end of a bone of a patient positioning a placement guide at an end of bone fragment reduced to a parent bone of a patient, the placement guide may include: a handle; a bone plate template that extends distally from the handle; two insertion guides each may include an opening configured to orient and guide a k-wire. The method includes deploying two k-wires into the bone fragment and into the parent bone by way of the two insertion guides; disengaging the placement guide from the two k-wires, drilling a first opening that circumscribes one of the two k-wires and a second opening that circumscribes the other one of the two k-wires using a cannulated drill bit, coupling two hooks of the hook plate with the two k-wires by way of alignment features of the hooks, sliding the hook plate along the two k-wires by way of the hooks such that the hooks move at least partially into the first opening and the second opening, and fixating the hook plate to the parent bone by deploying a fastener that engages the parent bone and the hook plate.

Implementations may include one or more of the following features. A method in which sliding the hook plate along the two k-wires further may include sliding the hook plate toward the parent bone by way of an inserter coupled to the hook plate and the method further may include disengaging the hook plate from the inserter and where the first opening and the second opening each have a diameter greater than an outer diameter of each of the hooks of the hook plate. The first opening and the second opening each extend into bone of the patient for a first distance greater than a second distance between a distal end of each of the hooks and an apex of the hooks.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings.

Figure 1:
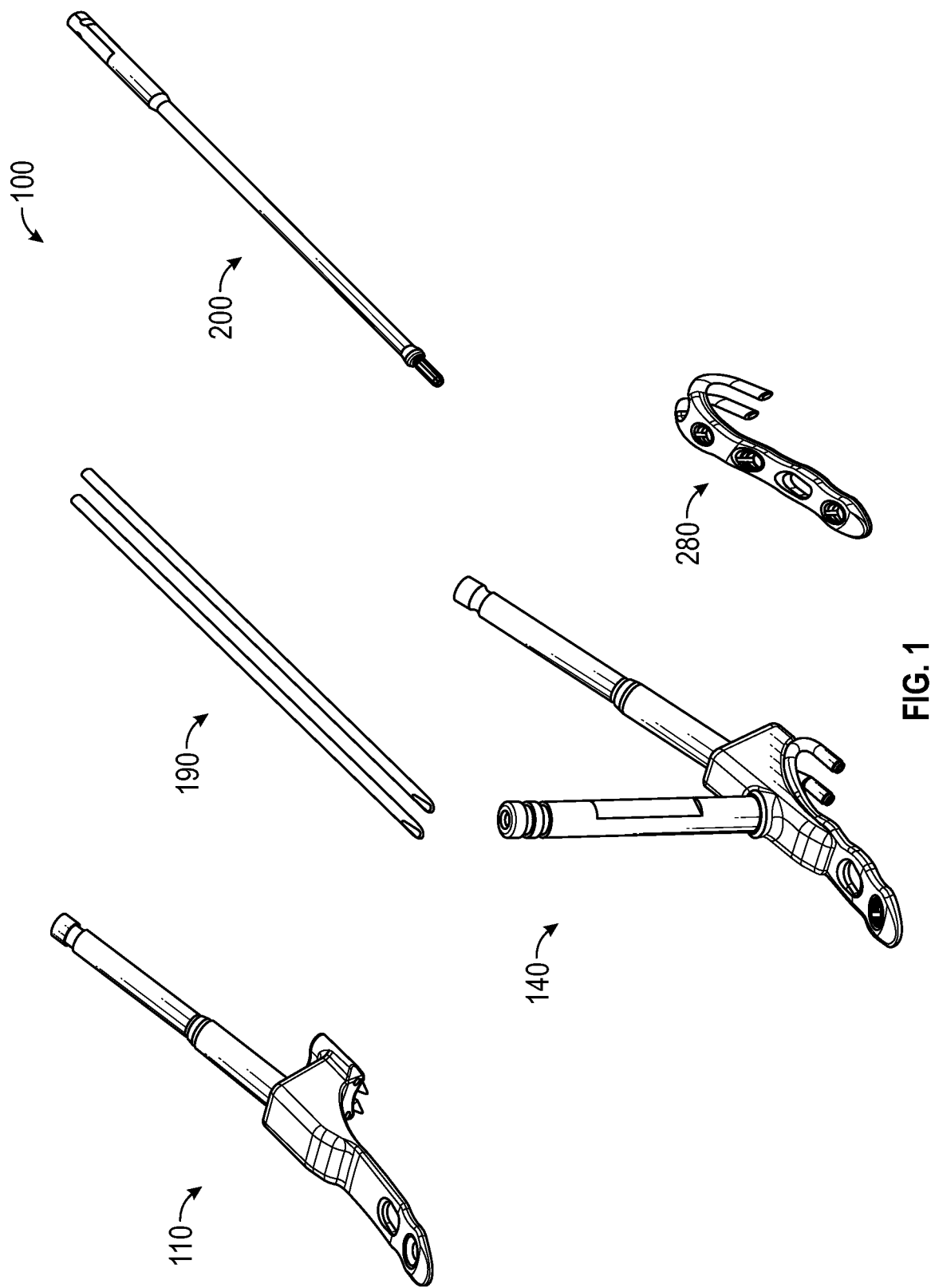
FIG. 1 is a perspective view of a hook plate system, according to one embodiment.

It is to be understood that the drawings are for purposes of illustrating the concepts of the disclosure and may or may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application but is merely representative of exemplary embodiments of the present disclosure.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular. Anterior means toward the front of a body.

Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user, viewer, or operator. Distal means away from the trunk. Distal may also mean away from a user, viewer, or operator. Dorsal means toward the top of the foot. Plantar means toward the sole of the foot. Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "preoperative" or "PRE-OP" refers to any activity, method, feature, or aspect performed before a surgical procedure. As used herein, "intraoperative" or "INTRA-OP" refers to any activity, method, feature, or aspect performed during a surgical procedure. As used herein, a "fixation" or "fixation device" refers to an apparatus, instrument, structure, device, component, member, system, assembly, step, process, or module structured, organized, configured, designed, arranged, or engineered to connect two structures either permanently or temporarily. The two structures may be one or the other or both of man-made and/or biological tissues, hard tissues such as bones, teeth or the like, soft tissues such as ligament, cartilage, tendon, or the like. In certain embodiments, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires (K-wires), screws, anchors, bone anchors, plates, bone plates, intramedullary nails or rods or pins, implants, interbody cages, fusion cages, and the like.

As used herein, "feature" refers to a distinctive attribute or aspect of something. (Search "feature" on google.com. Oxford Languages, 2021. Web. 20 Apr. 2021.) In certain embodiments, a feature may refer to a set of functions, actions, activities or aspects of a certain module, apparatus, device, and/or system. A feature may include one or more modifiers that identify one or more particular functions, attributes, advantages, aspects, or operations and/or particular structures relating to the feature. Examples of such modifiers applied to a feature, include, but are not limited to, "attachment feature," "securing feature," "alignment feature," "adjustment feature," "guide feature," "protruding feature," "engagement feature," "fixation feature", "disengagement feature," "resection feature," "guide feature," "anchor feature," and the like.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Cortical bone" refers to a type of bone tissue. Cortical bone is a type of bone tissue typically found between an external surface of a bone and an interior area of the bone. Cortical bone is more dense and typically stronger structurally than other types of bone tissue.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid.

In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body.

Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like. In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft. In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like. In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, "attribute" refers to any property, trait, aspect, quality, data value, setting, or feature of an object or thing.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Various conditions may adversely affect skeletal joints such as the injury, disease, deterioration, elongation, shortening, or rupture of soft tissues, cartilage, and/or bone associated with the joint and consequent laxity, pain, loss of movement, and/or deformity. As mentioned, a variety of procedures can be used to address these conditions, including: various osteotomy procedures, joint fusion procedures, fracture fixation procedures, joint resurfacing procedures, implants, joint spacers, and the like. Such procedures can be performed throughout the body and on various joints of the body.

However, these procedures, devices, and/or system have limitations. For example, certain procedures may remove a high percentage of bone of an articular surface of the joint. Other procedures may fuse the joint which may address pain but can limit mobility and activity of the patient. Other procedures and/or prosthesis may be prone to periprosthetic fractures and/or prosthetic dislocation.

The present disclosure discloses an improved hook plate apparatus, system, and method that is contoured to a bone surface of both the parent bone and the bone fragment, securely engages a bone fragment, wraps around a free end of the bone fragment, compresses the reduced fracture, extends from a surface of a bone fragment a minimal amount, and can be readily deployed using a guide feature. The hook plate apparatus, system, and method deploys the hook plate such that one or more hooks of the plate seat within openings in the bone fragment using openings that can be readily identified using the guide feature and with minimal, or no, tamping of the hooks to seat them within the openings. Alternatively, or in addition, the openings can be formed within a surface of the bone fragment furthest away from the fracture (e.g. a distal end of the bone fragment when in a reduced position).

FIG. 1 is a perspective view of a hook plate system 100 according to one embodiment. The hook plate system 100 can be used to secure a variety of bone fragments for fixation and/or healing on ends of a variety of bones within the body of a patient. Examples of bones with ends and/or named parts of bones where the hook plate system 100 can be used include, but are not limited to the femur, tibia, the fibula, radius, ulna, hand bones, foot bones, hip bones, shoulder bones, and the like. Additionally, the hook plate system 100 can be used to address a variety of different kinds of bone fractures, including but not limited to, a jones fracture, a pseudo-jones fracture, facture of the lateral malleolus, facture of the medial malleolus, a lisfranc fracture, an avulsion fracture, or the like.

"Bone fracture" refers to a medical condition in which there is a partial or complete break in the continuity of a bone. The bone may be broken into one or more pieces. (Search "bone fracture" on Wikipedia.com Apr. 21, 2022. CC-BY-SA 3.0 Modified. Accessed Jun. 10, 2022.) Bone fractures can be of one or more types. The name and/or type of fracture can be based on the specific bone involved, the condition of the bone due to the fracture, the type of bone, among other factors. Bone fractures may be closed/simple fractures or open/compound fractures. Bone fractures may be described as non-displaced or displaced. Bone fractures have a specific pattern such as a linear fracture, a transverse fracture, an oblique fracture, a spiral fracture, a compression/wedge fracture, an impacted fracture, and an avulsion fracture. Bone fractures may be incomplete fractures, complete fractures, and comminuted fractures. Bone factures of bones in the foot may be referred to as a lisfranc fracture (one or more metatarsals displaced from the tarsus), jones fracture (fracture of the proximal end of the 5th metatarsal), pseudo-jones fracture (fracture of the proximal end of the 5th metatarsal that includes an articular surface of the base of the 5th metatarsal), march fracture (fracture of the distal third of a metatarsal), cuneiform fracture (fracture of one of the cuneiform bones), calcaneal fracture (fracture of the calcaneus). (Search "bone fracture" on Wikipedia.com Apr. 21, 2022. CC-BY-SA 3.0 Modified. Accessed Jun. 10, 2022.) "Avulsion fracture" refers to a bone fracture in which part of a bone is torn or ripped away from another bone part. Avulsion fractures are most common where a tendon or ligament connects to a bone. (Search "avulsion fracture" on mayoclini.org Jun. 3, 2022. "Avulsion fracture: How is it treated?" Edward R Laskowski, M.D. Modified. Accessed Jun. 10, 2022.) "Bone fragment" refers to a part of a bone that is normally part of another bone of a patient. A bone fragment may be separate from another bone of a patient due to a deformity or trauma. In one aspect, the bone the bone fragment is normally connected or joined with is referred to as a parent bone. "Parent bone" refers to a bone is disconnected (partially or wholly) from a bone fragment. A parent bone may become separated from a bone fragment due to a deformity or trauma.

In one embodiment, the hook plate system 100 includes a placement guide 110, an inserter 140, at least one guide feature 190, a drill bit 200, and a hook plate 280. "Placement guide" refers to a guide that is designed, adapted, configured, or engineered to facilitate placement or deployment of an object, instrument, or implant into, onto, or in another relationship to another object. In one aspect, a placement guide may be used to guide insertion of an implant or fastener into a body part of a patient. As used herein, an "inserter" refers to an apparatus, instrument, structure, device, component, system, or assembly that is structured, organized, configured, designed, arranged, or engineered to insert or deploy one or more components, parts, or devices. In certain embodiments, an inserter can be used to insert implants and/or prosthesis into tissue, organs, or parts of a patient. In certain embodiments, an inserter can also be used to extract, retract, reposition, or remove an implant and/or prosthesis. The components of the hook plate system 100 cooperate to enable a surgeon to deploy and secure the hook plate 280 to compress and secure a bone fragment to the parent bone.

The placement guide 110 enables a surgeon to visualize how and where a hook plate 280 will sit on the patient before the hook plate 280 is deployed. In certain embodiments, the placement guide 110 also facilitates the placement or deployment of one or more guide features 190. Advantageously, with the placement guide 110 a surgeon can determine where fasteners can be placed within the hook plate 280 without using the actual hook plate 280. The placement guide 110 is configured to enable the surgeon to see the profile and permitter of the hook plate 280 without using an actual hook plate (e.g., one that has hooks).

In certain embodiments, the hook plate system 100 includes at least two guide features 190. The guide features 190 can be configured to extend through the bone fragment, across a bone fracture, and into a parent bone of the bone fragment. The guide features 190 can be implemented in a variety of ways. In one embodiment, the guide features 190 are two or more wires, fasteners, or pins, such as K-wires. The guide features 190 serve to guide the deployment of the hook plate 280. The drill bit 200 can serve to drill openings in the bone fragment. The drill bit 200 can be canulated such that the drill bit 200 fits over and is guided by the guide features 190. The openings drilled by the drill bit 200 can be configured to accept and/or receive one or more hooks of the hook plate 280.

The inserter 140 serves to facilitate deployment of the hook plate 280. In one embodiment, the inserter 140 releasably engages the hook plate 280 such that a surgeon operating the inserter 140 can insert the hook plate 280 into a prepared position on a bone of a patient. Alternatively, or in addition, the inserter 140 can also serve to facilitate drilling of pilot holes for fasteners and/or the deployment of the fasteners (e.g., bone screws).

The hook plate 280 serves to secure a bone fragment to parent bone with a fracture reduced. In certain embodiments, the hook plate 280 can wrap around an end of the bone. The hook plate 280 may include a plurality of fastener openings configured to accept fasteners. The hook plate 280 may include hooks that hold the bone fragment in place. In one embodiment, the hooks are cannulated and therefore include a cannula. Alternatively, or in addition, the hook plate 280 can include a fastening system configured to compress the bone fragment against the parent bone to promote healing.

Figure 2A:
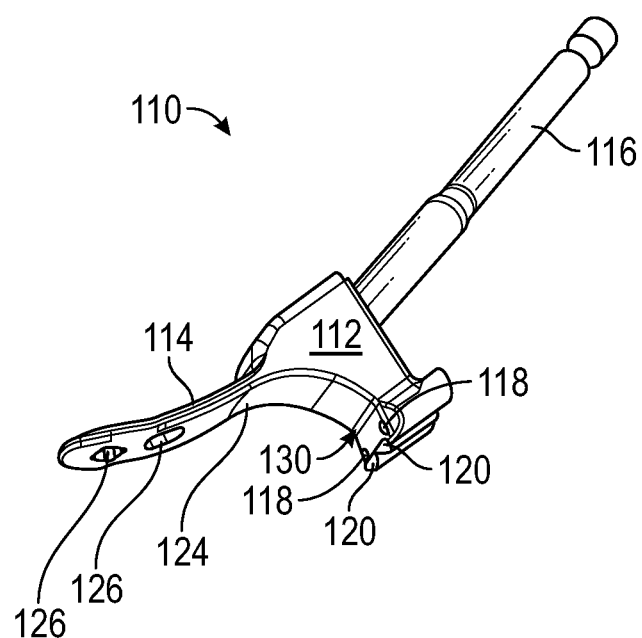
FIG. 2A is a perspective view of a placement guide and guide features, according to one embodiment.

FIG. 2A is a perspective view of a placement guide 110 and guide features, according to one embodiment. The placement guide 110 includes a placement body 112, a bone plate template 114, a handle 116, one or more insertion guides 118, and one or more engagement features 120. The placement body 112 can connect or may be integrated with the bone plate template 114 and/or handle 116.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide".

"Placement guide" refers to a guide that is designed, adapted, configured, or engineered to facilitate placement or deployment of an object, instrument, or implant into, onto, or in another relationship to another object. In one aspect, a placement guide may be used to guide insertion of an implant or fastener into a body part of a patient. "Template" refers to a part, component, member, tool, guide, or structure designed, adapted, configured, or engineered to show a user how another object can be positioned, sized, or oriented, with respect to another object. A template may serve as a guide. A template may be part of, integrated with, connected to, attachable to, or coupled to, another structure, device, or instrument. In one embodiment, a template may include a modifier that identifies a particular function, location, orientation, operation, type, and/or a particular structure for which the template is serving as an example or guide. Examples of such modifiers applied to a template, include, but are not limited to, "bone plate template" that identifies how a bone plate might fit, sit, or be oriented on a bone of a patient, a "fastener template" that identifies how a fastener might fit, sit, or be oriented when deployed in a patient, and the like. Furthermore, templates may include modifiers applied due to the procedure or location within a patient for which the template is to be used. For example, where a template is used for fixation of a bone, the template may be referred to herein as an "fixation template." In one aspect, the template refers to a template configured, designed, and/or engineered to serve as a template for creating, generating, or fabricating a patient specific implant or instrument. In one aspect, the template may be used, as-is, without any further changes, modifications, or adjustments and thus become a non-patient-specific template. In another aspect, the template may be modified, adjusted, or configured to more specifically address the goals, objectives, or needs of a patient or a surgeon and by way of the modifications become a patient-specific template.

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

Figure 2B:
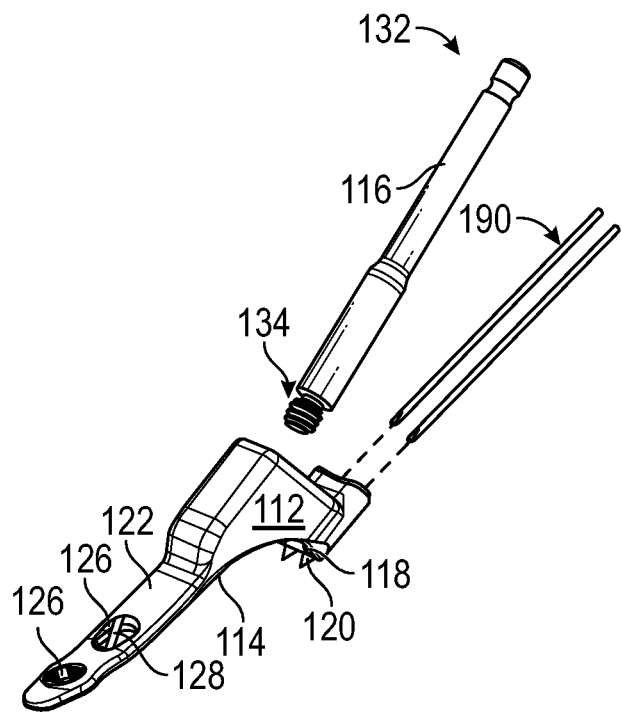
FIG. 2B is a perspective exploded view of a placement guide, according to one embodiment.

FIG. 2B is a perspective exploded view of placement guide 110, according to one embodiment. The bone plate template 114 may extend distally away from the placement body 112. Referring to FIGS. 2A and 2B, a superior surface 122 and an inferior surface 124 of the bone plate template 114 can be seen. Advantageously, the size, shape, and configuration of the bone plate template 114 may match or substantially match the attributes of at least a portion of a hook plate 280 that the surgeon has decided to deploy. In this manner, as a surgeon places and positions the placement guide 110 into the desired location and orientation, the surgeon can see how the hook plate 280 will sit when deployed. The surgeon may use the bone plate template 114 as a guide to understand whether the hook plate 280 will be of the desired size, shape, and configuration for this patient's anatomy.

To further assist a surgeon in understanding how the hook plate 280 will be deployed, the bone plate template 114 may further include one or more fastener templates 126. The one or more fastener templates 126 are configured to identify a location for a fastener of the hook plate 280. In one embodiment, the fastener templates 126 may be sized, configured, and positioned in the same locations as fastener openings in the hook plate 280. The fastener templates 126 can serve as landmarks for the hook plate 280 so that the surgeon can evaluate how fasteners in the fastener openings of the hook plate 280 will engage with the bone of the patient. In certain embodiments, a surgeon may be reminded, or instructed, not to use the fastener templates 126 to drill pilot holes and/or to deploy fasteners, either temporarily or permanently.

The fastener templates 126 may be open or closed. An open fastener template 126 is a fastener template 126 having an opening that passes from the superior surface 122 to the inferior surface 124. A closed fastener template 126 is a fastener template 126 that includes a feature the prevents use of the fastener template 126 for deployment of a fastener. In one embodiment, this feature may be a stop 128 that partially or wholly blocks an opening of the fastener template 126. The stop 128 can be configured to interfere with the insertion of a fastener into an opening in the fastener template 126.

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

In the illustrated embodiment, the stop 128 is a cross beam over an opening in fastener template 126. Alternatively, or in addition, a stop 128 can be an opening in the fastener that does not extend completely through from the superior surface 122 to the inferior surface 124, a protrusion, or the like.

In certain embodiments, the inferior surface 124 is configured to match at least a portion of an inferior surface of a hook plate 280. In this manner, as a surgeon places, orients and/or reorients the placement guide 110, the surgeon can see, and/or feel, how the hook plate 280 will rest on the peritoneum, the chondral structures, an exposed surface of the bone (e.g. parent bone and/or bone fragment), and/or structures. In certain embodiments, the inferior surface 124 includes substantially the same contour as the inferior surface of the hook plate 280.

Alternatively, or in addition, the inferior surface 124 can be configured such that at least a portion 130 of the inferior surface 124 that is near, or closest to, a proximal end of the inferior surface 124 can abut the bone fragment (when reduced to the parent bone). Said another way, the proximal end of the inferior surface 124 may include no hooks that could otherwise interfere with placement of the inferior surface 124 against the bone in the same manner as the hook plate 280 will sit when the hook plate 280 is deployed. This is advantageous because the placement guide 110 can be used before any holes have been drilled in bones of the patient, and yet the surgeon can trial where and how the hook plate 280 will eventually sit on the bone(s).

The insertion guides 118 serve to guide the insertion of one or more fasteners. In one embodiment, the placement guide 110 includes at least two insertion guides 118 and the insertion guides 118 are parallel to each other. In the illustrated embodiment, the insertion guides 118 are implemented as openings in the placement body 112 proximal to an inferior side of the placement body 112. The openings may extend from one side (e.g., a proximal side) to an opposite side (e.g., a distal side) of the placement body 112. In one embodiment, the insertion guides 118 orient and/or guide two guide wires as the guide wires are inserted into and engage a bone fragment. "Guide wire" refers to a type of fastener that can be used to guide an instrument or implant as part of a method, process, or procedure, such as a surgical technique. In certain aspects, a guide wire may be designed for temporary use until subsequent steps in a method, process, or procedure. Examples of a guide wire include, but are not limited to, a pin, a K-wire, and the like.

In the illustrated embodiment, each opening has a circular cross section and are sized to accommodate a guide feature 190, such as a 1.5 mm-3 mm diameter K-wire. The insertion guides 118 are positioned in the placement body 112 such that guide features 190 deployed using the insertion guides 118 will be in a desired position in bone of the patient for deployment of the hook plate 280.

The placement guide 110 may also include one or more engagement features 120. "Engagement member" refers to an apparatus, instrument, structure, device, component, member, system, assembly or module structured, organized, configured, designed, arranged, or engineered to connect, join, link, couple to, or engage with another object, apparatus, instrument, structure, device, component, member, system, assembly or module either permanently or temporarily. The connection, coupling, linkage, or engagement may be a mechanical connection or interconnection.

The engagement features 120 can help a surgeon in securing the placement guide 110 against a bone fragment and in retaining a bone fragment in a reduced condition as the guide features 190 is in use. In one embodiment, the engagement features 120 may be spikes or prongs and may be positioned proximal to an inferior side of the placement body 112. The engagement features 120 may extend from the inferior surface 124 of the placement body 112 between about 0.5 mm and 2 mm. In the illustrated embodiment, the engagement features 120 are parallel to each other.

FIG. 2B illustrates the handle 116. The handle 116 can include a proximal end 132 and a distal end 134. The proximal end 132 may include an AO quick connect interface that allows a surgeon, or other user, to attach a preferred handle grip at the proximal end 132 of the handle 116. The distal end 134 may include a set of external threads configured to engage with internal threads of an opening in the placement body 112.

Figure 2C:
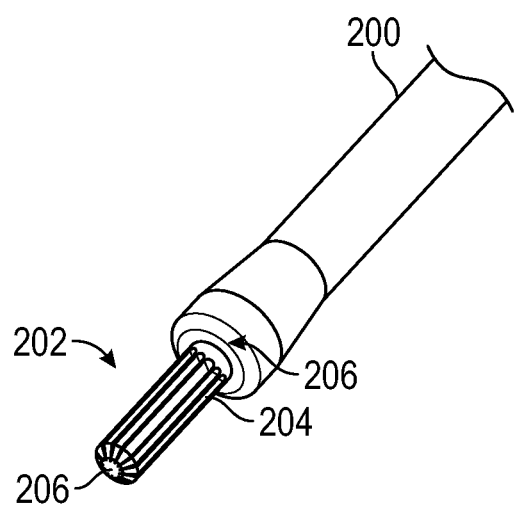
FIG. 2C is a perspective close up view of a drill bit, according to one embodiment.

FIG. 2C is a perspective close up view of a drill bit 200, according to one embodiment. The drill bit 200 serve to form openings in bone of the patient, in particular, in the bone fragment. In the illustrated embodiment, the drill bit 200 includes a distal end 202 that includes one or more flutes 204. All, or part, of the drill bit 200 may be cannulated such that an opening 206 extends coaxial to a longitudinal axis of the drill bit 200. In certain embodiments, the drill bit 200 may include a stop 208 where the flutes 204. The stop 208 can serve to control how deep the opening is drilled into the bone. "Cannulated drill bit" refers to a drill bit, often a surgical drill bit, that includes a tube or opening in the drill bit. In certain embodiments, a tube or opening through the drill bit is coaxial with the drill bit.

Figure 3A:
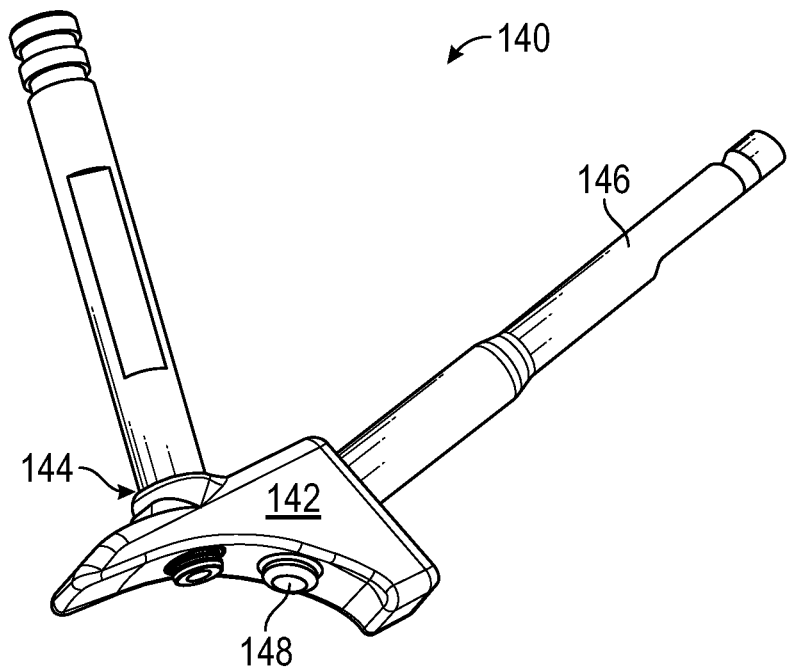
FIG. 3A is a perspective view of an inserter, according to one embodiment.

FIG. 3A is a perspective view of an inserter, according to one embodiment. The inserter 140 includes an inserter body 142 and a coupler 144. The inserter body 142 provides structural support for other members of the inserter 140. In one embodiment, the coupler 144 extends proximally from a hook plate 280 engaged by the inserter 140. The coupler 144 serves to connect and/or disconnect the inserter 140 from a hook plate 280 as part of deploying the hook plate 280. In certain embodiments, the inserter 140 can include a handle 146. As used herein, "coupling", "coupling member", or "coupler" refers to a mechanical device, apparatus, member, component, system, assembly, or structure, that is organized, configured, designed, arranged, or engineered to connect, or facilitate the connection of, the two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semiflexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

The inserter body 142 may include one or more protrusions 148. A protrusion 148 may facilitate engagement between the inserter body 142 and the hook plate 280.

Figure 3B:
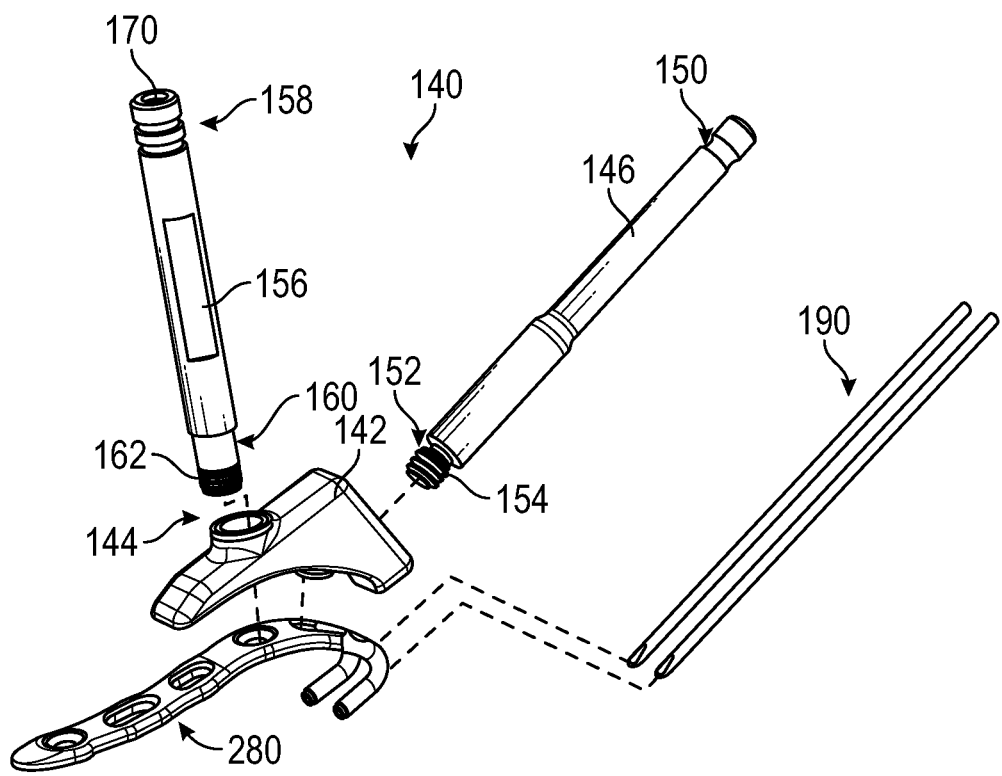
FIG. 3B is a perspective exploded view of an inserter, hook plate, and guide features, according to one embodiment.

FIG. 3B is a perspective exploded view of the inserter 140, hook plate 280, and guide features 190, according to one embodiment. The exploded view illustrates certain details of handle 146 and coupler 144. In the illustrated embodiment, the handle 146 has a proximal end 150 and a distal end 152 with external threads 154 at, or near, the distal end 152. The proximal end 150 may be an AO quick connect interface. The external threads 154 may be configured to engage internal threads of an opening on a proximal side of the inserter body 142.

Referring to FIGS. 3A and 3B, those of skill in the art will appreciate that the coupler 144 can be implemented in a variety of ways. The coupler 144 serves to releasably engage the hook plate 280. In one embodiment, the coupler 144 may include a knob connected to a shaft having distal external threads, the shaft configured to pass through an opening in the inserter body 142 and engage internal threads of an opening in the hook plate 280. In certain embodiments, the opening in the hook plate 280 may be a fastener opening used for fixating the hook plate 280 to the bone as part of the procedure.

In the illustrated embodiment, the coupler 144 may include a drill guide 156 having a proximal end 158 and a distal end 160 having external threads 162 configured to engage internal threads of a fastener opening of the hook plate 280. The distal end 160 may have a larger diameter than an opening in the inserter body 142 such that as the external threads 162 engage internal threads of a fastener opening the inserter body 142 is compressed between the drill guide 156 and the hook plate 280. In this manner, the hook plate 280 can be coupled to the inserter body 142 as the hook plate 280 is deployed. Similarly the drill guide 156 can be rotated in a direction to disengage the external threads 162 such that the hook plate 280 is released from the inserter body 142 and the drill guide 156.

The drill guide 156 may be cannulated, may have a coaxial internal opening 170 that extends from the proximal end 158 to the distal end 160. The opening 170 may be configured to accept a drill bit which a surgeon can use to drill a pilot hole and/or to drive a fastener into a bone. The opening 170 may align with a fastener opening in the hook plate 280.

FIG. 3B illustrates that the protrusion 148 may be configured to fit within an open space of the hook plate 280. "Open space" refers to an area within, surrounded by, or between two structures that is void of any structures or objects. The guide features 190 may engage with a proximal end of the hook plate 280 and guide the hook plate 280 and inserter 140 as the hook plate 280 is deployed.

Figure 4B:
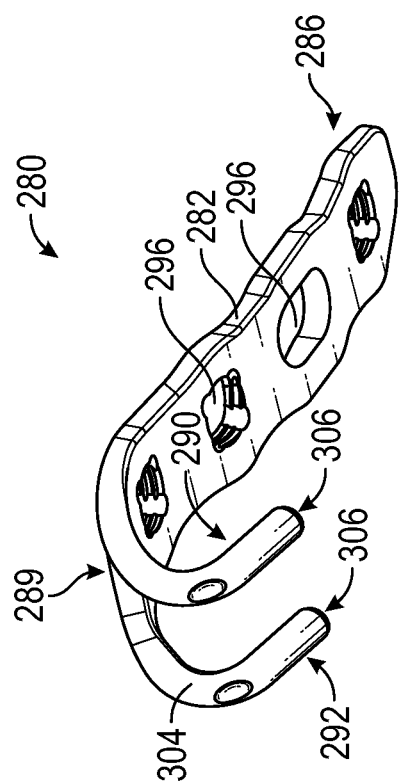
FIG. 4B is another perspective view of the implant of FIG. 4A according to one embodiment.
Figure 4A:
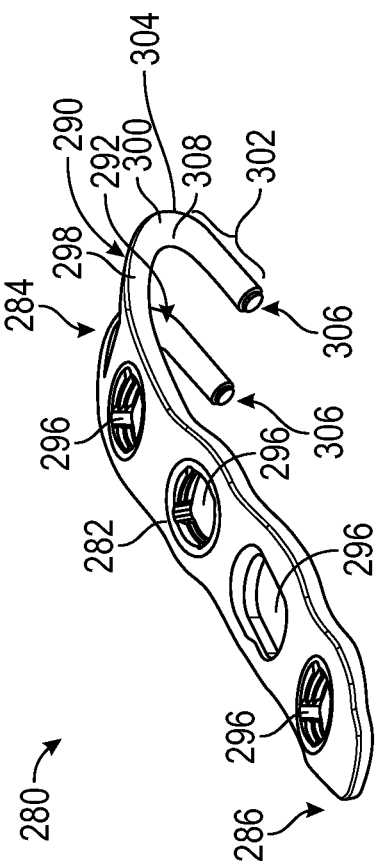
FIG. 4A is a perspective view of an implant according to one embodiment.

FIG. 4A is a perspective view of an implant according to one embodiment. In the illustrated embodiment, the implant is a hook plate 280. The hook plate 280 includes a body 282 that extends between a proximal end 284 and a distal end 286, a first hook 290, and a second hook 292. One or more of the first hook 290 and/or the second hook 292 are configured to slidably engage with an alignment feature 306. The alignment feature 306 guides one or more of the first hook 290 and/or the second hook 292 into an opening in the bone of a patient.

The first hook 290 and second hook 292 may define an open space 294 between them. The hook plate 280 may include one or more fastener openings 296. The fastener openings 296 may be of a variety of types. For example, one or more of the fastener opening 296 may be a compression opening for a compression fastener assembly.

One or more hook(s) of the hook plate 280 may include a base 298, a bend 300, and a prong 302. "Hook" refers to a structure or tool consisting of a length of material that contains a portion that is curved or indented, such that the portion can be used to grab onto, connect, or otherwise engage another object. In certain embodiments, one end of the hook can be pointed, so that this end can pierce another material, which may then be held by the curved or indented portion. (Search "hook" on Wikipedia.com Apr. 18, 2022. CC-BY-SA 3.0 Modified. Accessed Jun. 10, 2022.) In certain embodiments, the curved or indented portion may be referred to as a bend. The bend may connect to a free end of the hook that may be referred to as a prong 302. "Prong" refers to a structure that extends from another structure. Often a prong is elongated and may come to a point at the end. A prong may also be referred to as a hook, a spike, tine, point, tip, fork, projection, spur, barb, or the like.

The base 298 extends proximal to the proximal end 284. As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position.

The bend 300 connects the base 298 and the prong 302. The prong 302 may extend from the bend 300. In certain embodiments, the bend 300 may engage with bone fragment when the hook plate 280 is deployed. The bend 300 may include an apex 304. As used herein, "bend" refers to an angled or curved structure, or a part or a portion of a structure, that changes an orientation of the structure. The structure that includes the bend can be a pipe, a tube, a cable, a hose, a sheet, a path, an opening, a portal, a building, a road, or the like. Typically, a bend changes an orientation of the structure at an angle between 0 and 180 degrees or between 180 degrees and 360 degrees along a longitudinal axis of the structure. The structure can include a single bend or a plurality of bends. "Apex" refers to a highest point on or along a curve. In certain embodiments, the bend 300 defines an acute angle between the base 298 and the prong 302. Alternatively, or in addition, the bend 300 may define a right angle between the base 298 and the prong 302. Alternatively, or in addition, the bend 300 may define an obtuse angle between the base 298 and the prong 302. In certain embodiments, the prong 302 is configured to engage a guide feature 190. In one embodiment, the prong 302 may slidably engage the guide feature 190 as the hook plate 280 is deployed and/or to facilitate deployment of the hook plate 280.

FIG. 4B is another perspective view of the implant of FIG. 4A according to one embodiment. In certain embodiments, the hook plate 280 may include an alignment feature 306. In one embodiment, one or more of the first hook 290 and/or the second hook 292 may include the alignment feature 306. Specifically, a prong 302 of the first hook 290 and/or the second hook 292 may include the alignment feature 306. The alignment feature 306 can facilitate alignment between the prong 302 and an opening in the bone. In certain embodiments, an alignment feature 306 may engage with a guide feature 190. In one embodiment, an alignment feature 306 may slidably engage a guide feature 190. The alignment feature 306 and guide feature 190 can cooperate to guide a hook into an opening in bone of the patient.

As used herein, an "opening" refers to a gap, a hole, an aperture, a port, a portal, a space or recess in a structure, a void in a structure, or the like. In certain embodiments, an opening can refer to a structure configured specifically for receiving something and/or for allowing access. In certain embodiments, an opening can pass through a structure. In other embodiments, an opening can exist within a structure but not pass through the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

Figure 4D:
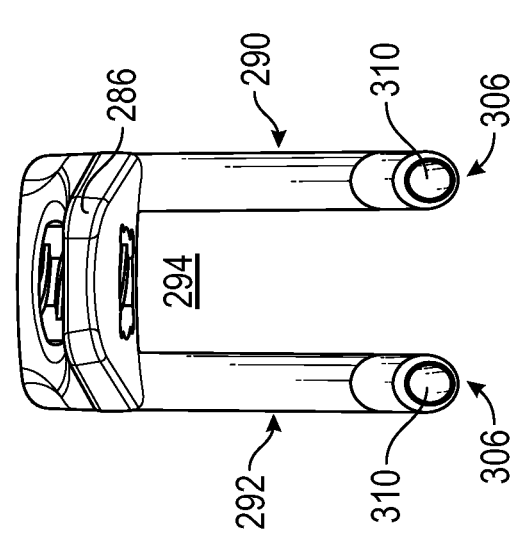
FIG. 4D is perspective view from a proximal end of the implant of FIG. 4A according to one embodiment.
Figure 4C:
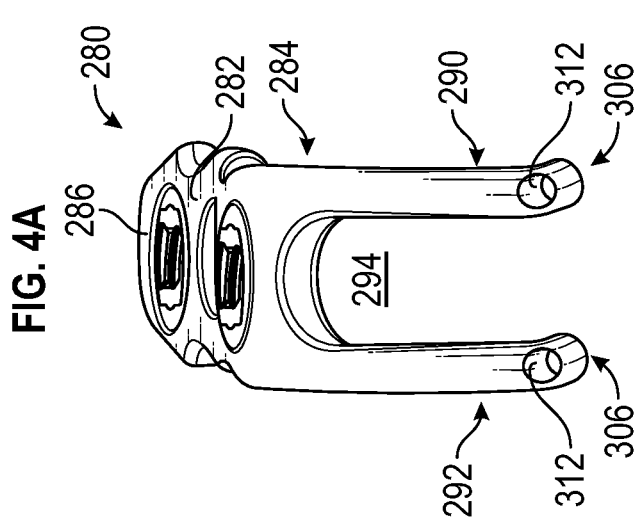
FIG. 4C is perspective view from a distal end of the implant of FIG. 4A according to one embodiment.

FIG. 4C is perspective view from a proximal end of the implant of FIG. 4A according to one embodiment. FIG. 4D is perspective view from a distal end of the implant of FIG. 4A according to one embodiment. Those of skill in the art will appreciate that the alignment feature 306 may be implemented in a variety of ways. In the illustrated embodiment, the alignment feature 306 is a cannula 308. "Cannula" refers to a structure configured to enable passage of another structure, object, or fluid from a starting point to an ending point. When used in a medical context, a cannula can comprise a channel, a passage, a tube, a chamber, or a pipe that can be used to convey fluids into or out of a body of a patient. In certain embodiments, a cannula can serve to provide access to an internal part or area of a body of a patient through a minimally invasive opening in parts of the body. More generally, cannula can refer to any structure having two interconnected openings through which objects or fluids can be passed. The objects may be one or more of an implant, a fastener, an instrument, or the like.

The cannula 308 may include a first opening 310 near the prong 302 and a second opening 312 near the bend 300. In certain embodiments, the first opening 310 and second opening 312 may connect and together the space in the opening may be uniform in shape and may have a common diameter, referred to as a first diameter. In one embodiment, the first opening 310 and second opening 312 are configured to accept at least a portion of a guide feature 190. Consequently, the first diameter of the first opening 310 near the prong 302 and a second opening 312 is greater than a second diameter of the guide feature 190. In certain embodiments, the first opening 310 and second opening 312 may each have a circular cross section.

Since the cannula 308 is a tube shape, such an alignment feature 306 can ensure that once a guide feature 190 is inserted into the cannula 308, the cannula 308 and guide features 190 remain engages in a coaxial relationship. Initially passing the guide feature 190 through cannula 308 may take extra care and alignment, however once the guide features 190 passes through the cannula 308 the two structures remain slidably engaged.

In certain embodiments, the hook plate 280 may include a single hook (e.g., first hook 290). In another embodiment, the hook plate 280 may include two or more hooks (e.g., first hook 290 and second hook 292). A second hook 292 may extend parallel to, and aligned with, the first hook 290. The second hook 292 may also include an alignment feature configured to engage a second guide feature 190 to guide the second hook 292 into a second opening in the bone of the patient.

In certain embodiments, the first hook 290 and second hook 292 are positioned relative to each other so that they define an open space 294. The open space 294 can be used for a variety of purposes. As discussed above, the open space 294 may serve to receive a protrusion 148 of the inserter 140. Alternatively, or in addition, the open space 294 may also serve to engage with a fastener inserted into a bone fragment between the two hooks 290, 292 and within the open space 294. Advantageously, the two hooks 290, 292 may be configured so as to define the size of the open space 294 such that the shaft fits within the open space 294 and a head of a fastener contacts and presses against the two hooks 290, 292 as the fastener engages with the bone. Such a fastener may be referred to in the art as a homerun screw and may be used to provide cross fracture fixation and an extra fixation measure to couple a bone fragment to a parent bone.

Referring to FIGS. 4A-4D, the hooks of the hook plate 280 are configured to ensure secure engagement of a bone fragment reduced to the parent bone. In one embodiment, the hooks (e.g., first hook 290 and second hook 292) extend from the proximal end 284 of the hook plate 280 and wrap around at least a portion of an end of bone (e.g., the bone fragment). In this manner, the hooks (e.g., first hook 290 and second hook 292) can provide a secure engagement with the bone. The alignment feature 306 can be positioned and/or connected to various locations on the hook plate 280. In the illustrated embodiment, an alignment feature 306 is proximal to the prong 302 of each hook. In certain embodiments, the alignment feature 306 is configured to slide linearly along a guide feature 190. In one embodiment, the alignment feature 306 slides linearly along a guide feature 190 and seats wholly within an opening in the bone. Alternatively, or in addition, the alignment feature 306 may be releasable from the hook plate 280 once the hook plate 280 is partially or wholly deployed.

In an example embodiment of FIGS. 4A-4D, the first hook 290 and second hook 292 are cannulated hooks proximal to a proximal end of the hook plate 280. The first and second cannulated hooks are parallel to each other and extend toward a distal end 286 of the hook plate 280 (e.g. the prongs 302 extend toward the distal end). "Cannulated hook" refers to a hook that includes at least a portion of the hook with a cannula formed therein or connected thereto. The cannulated hooks may each include a cannula 308 sized to slide along one of the guide features 190 (e.g. guide wires or K-wires) and at least partially into an opening in the bone. The opening extends at least into the bone fragment and may extend into the parent bone. The opening circumscribes a guide feature 190 (e.g. guide wire or K-wire).

Figure 5:
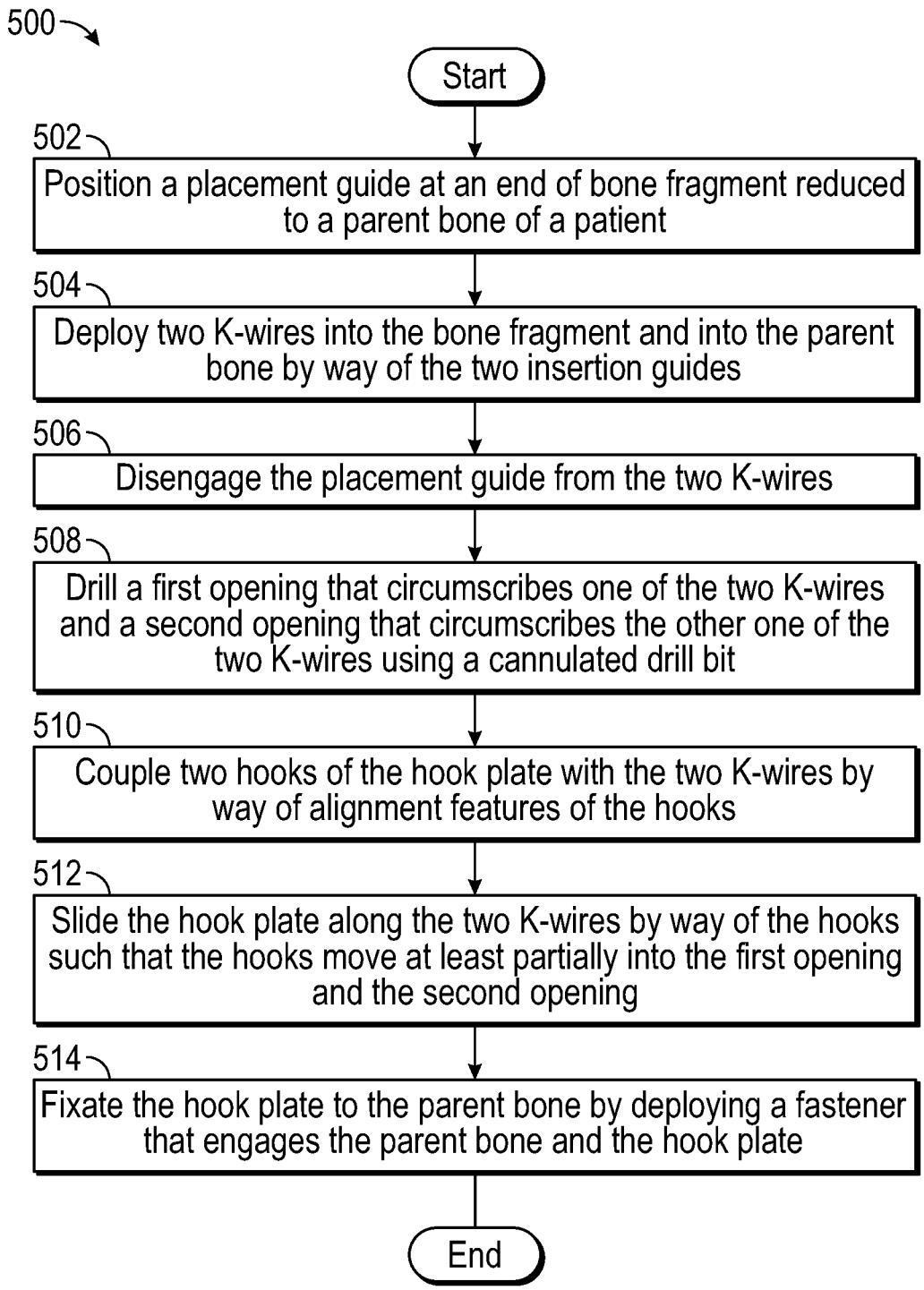
FIG. 5 is a flow chart diagram of one example method for using a hook plate system according to one embodiment.
Figure 6A:
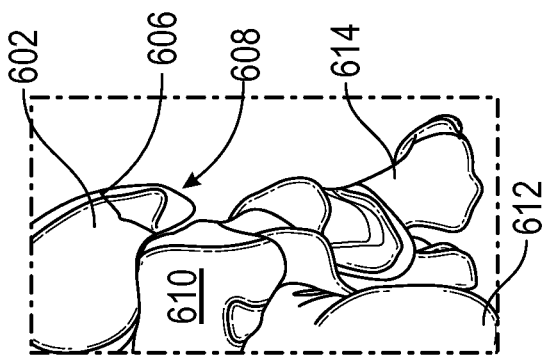
FIGS. 6A-6G illustrate perspective side views of different steps in an example method for deploying a hook plate system according to one embodiment.
Figure 6B:
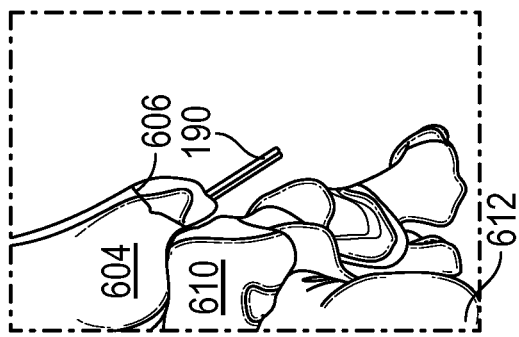

FIG. 5 is a flow chart diagram of one example method 500 for using a hook plate system according to one embodiment. FIGS. 6A-6G illustrate perspective side views of different steps in an example method, such as method 500 for deploying a hook plate system 100 according to one embodiment. FIG. 6A illustrates one location in a patient where the hook plate system 100 can be used. FIG. 6A illustrates a medial malleolus 602 of the tibia 604 with a bone fracture 606 proximal to the distal end 608 of the medial malleolus 602. FIG. 6A also illustrates the talus 610, calcaneus 612, and first metatarsal 614 for reference. In certain embodiments, the bones of the bone fracture 606 may be reduced as shown in FIG. 6A. Alternatively, or in addition, before or as part of a first step of the method 500 a surgeon may reduce the bones of the bone fracture 606.

Referring to FIGS. 5 and 6B through 6G, the method 500 starts and a user, such as a surgeon, may position 502 a placement guide 110 at an end (e.g., the distal end 608 in FIG. 6B) of a bone fragment 616 reduced to a parent bone 618 of a patient. Note that the placement guide 110 is placed in the same position as a hook plate 280 which will be deployed in a subsequent step. Although not shown, the handle 116 of the placement guide 110 may be covered by an AO quick connect handle during a procedure. The surgeon may use the handle 116 to press or hold the placement guide 110 against the bone fragment 616 and/or parent bone 618. The bone plate template 114 is shown resting on the peritoneum, or surface, of the parent bone 618. In addition, the insertion guides 118 are positioned to guide K-wires, or other fasteners, into the bone fragment 616. In the illustrated embodiment, the insertion guides 118 are positioned at a distal end 608 of the bone fragment 616.

Figure 6C:
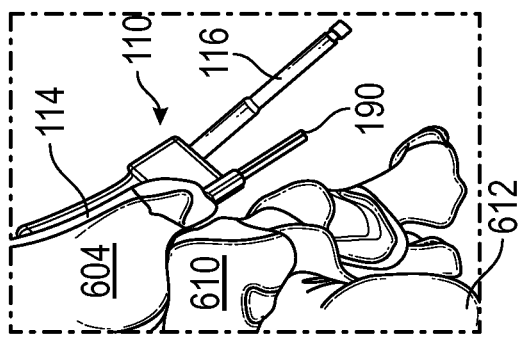

If a surgeon is satisfied with the position of the bone plate template 114, including any fastener templates 126, the method 500 may proceed to the next step. In the next step, the surgeon may deploy 504 one or more guide features 190 (e.g., K-wires) by way of the insertion guides 118. In the illustrated embodiment, the surgeon may drive K-wires through the insertion guides 118, into the bone fragment 616, and into the parent bone 618. FIG. 6C illustrates the condition after step 504. The guide features 190 are deployed into the bones and extend from the proximal side of the placement guide 110. The surgeon, or other user, may continue to hold the placement guide 110 in a position illustrated in FIG. 6C.

Figure 6D:
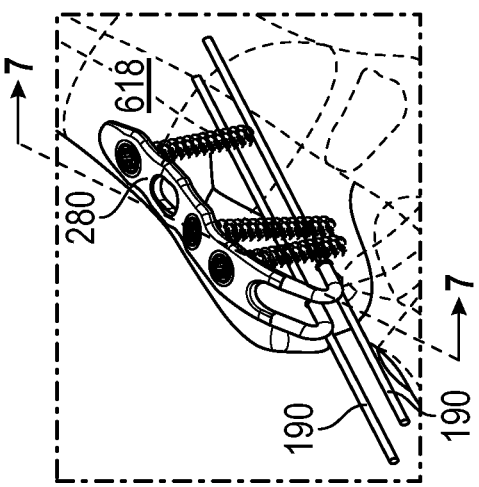

Next, a surgeon, or other user, may disengage 506 the placement guide 110 from the K-wires 190. FIG. 6D illustrates the condition after step 506, the bone fracture 606 is maintained in a reduced condition by the K-wires 190 and the placement guide 110 has been removed.

Figure 6E:
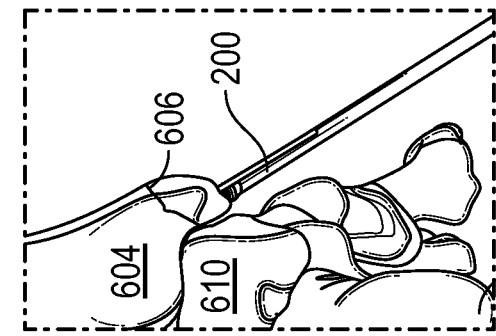

Next, a surgeon, or other user, may drill 508 a first opening that circumscribes one of the two K-wires and a second opening that circumscribes the other one of the two K-wires using a cannulated drill bit 200. In certain embodiments, the openings drilled extend approximately to a length of the prong 302. Alternatively, or in addition, the openings can be drilled for a depth greater than a length of the prong 302. The K-wires serve as guides for drilling the openings. In certain embodiments, the openings may extend through both the bone fragment 616 and the parent bone 618. Alternatively, or in addition, the openings may extend only through the bone fragment 616. FIG. 6E illustrates the condition during step 508, the bone fracture 606 is maintained in a reduced condition by the K-wires 190 and the drill bit 200 drills one of the openings.

Next, a surgeon, or other user, may couple 510 two hooks of a hook plate 280 to the K-wires 190. Next, a surgeon may slide 512 the hook plate 280 along the two K-wires 190 by way of the hooks such that the hooks move at least partially into the first opening and second opening. In certain embodiments, sliding 512 the hook plate 280 along the two K-wires may include sliding the hook plate 280 toward the parent bone 618 by way of an inserter 140 coupled to the hook plate 280. The method 500 may also include disengaging the hook plate 280 from the inserter 140. In certain embodiments, the first opening may have a diameter greater than an outer diameter of a hook of the hook plate 280 received by the first opening and the second opening may have a diameter greater than an outer diameter of a hook of the hook plate 280 received by the second opening.

Figure 6F:
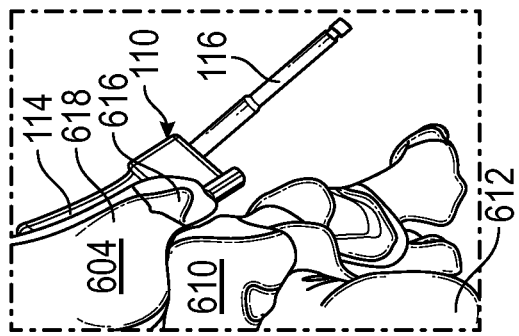

FIG. 6F illustrates the condition after step 512, the bone fracture 606 is maintained in a reduced condition by the K-wires 190 and the inserter 140 (which is coupled to the hook plate 280) is pressing against the distal end 608. The guide features 190 have assisted to ensure that the hooks of the hook plate 280 enter the first opening and second opening.

In certain embodiments, the surgeon may decouple the hook plate 280 from the guide features 190 and reengage a different hook plate 280 (for example a different size) to the guide features 190. In embodiment where the hook plate 280 includes an alignment feature 306 that is a cannula decoupling the hook plate 280 may include unthreading the alignment feature 306 from the guide features 190. However, in embodiments that include an alignment feature 306 that does not fully encircle the guide features 190 (e.g. a half-circle cannula), removing and replacing a hook plate 280 can be easier and quicker.

Note that in FIG. 6F the inserter 140 may include a different coupler 144 than the embodiment described above. The coupler 144 in FIG. 6F may not include a feature for drilling a pilot hole in a fastener opening 296.

Figure 6G:
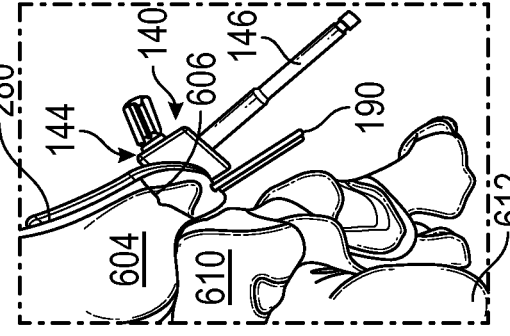

Next, a surgeon, or other user, may fixate 514 the hook plate 280 to at least one or more of the parent bone 618 and the bone fragment 616. This step 514 may be done, at least in part, by deploying one or more fasteners using one or more fastener openings 296 of the hook plate 280. FIG. 6G illustrates the condition after step 514, the bone fracture 606 is maintained in a reduced condition and the hook plate 280 is secured to the parent bone 618 and/or the bone fragment 616. As a surgeon is deploying the fixation, the surgeon may remove the K-wires 190 once the surgeon is comfortable doing so. For example, once doing so will not disturb the reduction.

In certain embodiments, the hook plate 280 may engage the bone fragment 616 solely by way of the hooks. Alternatively, or in addition, a fastener may connect to the hook plate 280 and the bone fragment 616. In another embodiment, another fastener (e.g., "homerun screw") may be deployed between the hooks at the distal end 608, within the open space 294. The head of the fastener may contact both hooks once deployed.

Figure 6H:
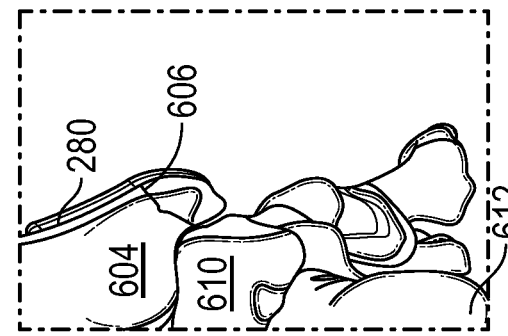
FIG. 6H is a perspective view of a deployed implant according to one embodiment.

FIG. 6H is a perspective view of a deployed implant (e.g., hook plate 280) according to one embodiment. FIG. 6H illustrates the condition after step 512 and before the K-wires 190 are removed. The bone fragment 616 and parent bone 618 are shown as transparent such that deployed fasteners can be seen. Advantageously, the guide features 190 (e.g., K-wires) maintain the reduced bone fragment 616 in a desired position throughout the surgical procedure. The guide features 190 can remain in place until all fixation fasteners have been deployed. In this manner, the integrity of the reduction is maintained and in a way that facilitates the surgical procedure for the surgeon.

Figure 7:
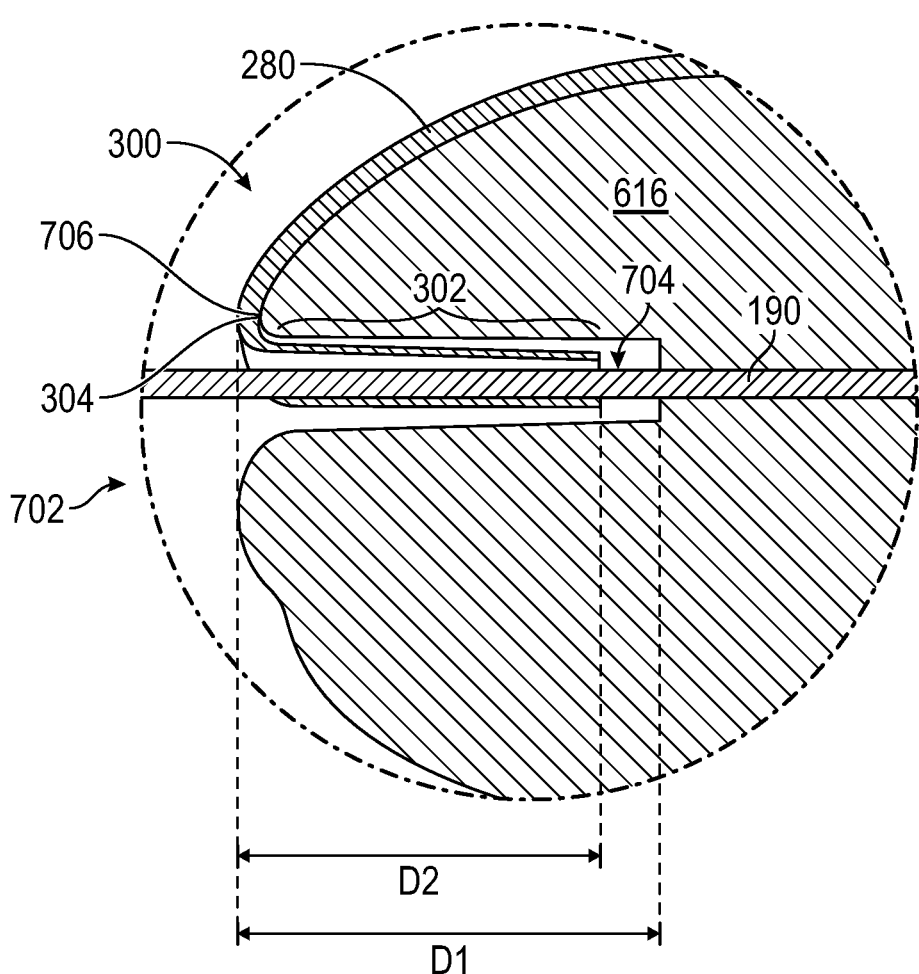
FIG. 7 is a cross-section view of a hook plate deployed within a bone according to one embodiment.

FIG. 7 is a cross-section view of a hook plate 280 deployed within a bone according to one embodiment taken along line 7-7 of FIG. 6H-. FIG. 7 illustrates an opening 702 in cross-section, a prong 302 in cross-section, a bend 300 in cross-section, a base 298 in cross-section, a guide feature/wire 190 in cross-section, and the bone fragment 616 in cross-section. As discussed above, the guide feature 190 guides a hook into the opening 702 such that the bend 300 contacts the bone fragment 616 proximal to the opening 702. In certain embodiments, the prong 302 may not extend past an open side of the opening 702.

The opening 702 may extend into the bone fragment 616 for a first distance D1 (e.g., 4-7 mm). The prong 302 may fit completely within the opening 702. A distal end 704 of the prong 302 may extend from the bend 300 a second distance D2 from the apex 304 of the hook to the distal end 704. The second distance D2 may be shorter than the first distance D1. Said another way, the opening 702 extends into bone fragment 616 for a length that is greater than the distance a prong 302 of the hook can extend into the opening 702. This configuration facilitates minimizing the distance an implant, like the hook plate 280 extends beyond the distal end 608 of the bone. Those of skill in the art will appreciate that the opening 702 is representative of one or mor openings in the bone fragment 616.

Advantageously, this difference in distances can result in an alignment feature 306 having little to no influence on the strength and integrity of the hook with respect to holding the bone fragment 616 in place. Instead, the compression force of the hook plate 280 may press against the bone near the 702 by way of the bend 300 contacting the bone; for example, at contact point 706. In addition, the alignment feature 306 may not extend distally beyond the distal end 608 of the bone (e.g., bone fragment 616). In this manner, the profile of the hook of the hook plate 280 at the distal end 608 is minimized. For example, the profile of the hook may extend no more than the thickness of the hook through the bend 300.

FIGS. 8A-8J illustrate cross-section views of different embodiments of an alignment feature according to various embodiments. FIGS. 8A-8J each illustrate an example embodiment that includes two parallel hooks of a hook plate according to the present disclosure. The cross-section is taken across the two prongs 302 of the hooks. Each FIG. of FIGS. 8A-8J illustrate a cross-section of the guide features 190 and an example alignment feature 306 having the illustrated configuration.

Figure 8A:
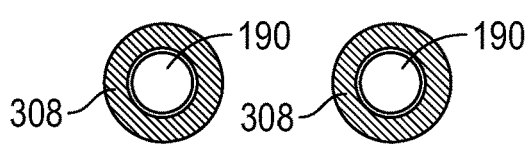
FIGS. 8A-8J illustrate cross-section views of different embodiments of an alignment feature according to various embodiments.
Figure 8B:
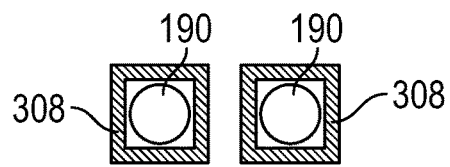

FIG. 8A illustrates an embodiment in which the alignment feature 306 comprises a cannula 308. FIG. 8A illustrates that the cannula 308 circumscribes the alignment feature 306 for both hooks. The cannula 308 of FIG. 8A has a circular cross-section. Of course, the cannula 308 can also have a polygonal cross section. FIG. 8B illustrates an example of a polygonal cannula 308.

One should note that the alignment feature 306 can have a variety of configurations and the configuration of the alignment feature 306 can vary between hooks. For example, the alignment feature 306 may include a groove 802 (See FIG. 8B) that extends along at least a portion of the first hook 290 and/or second hook 292. In certain embodiments, the groove 802 may extend from a free end of the prong 302 to the bend 300. "Groove" refers to an indentation built into a material. In some implementations, a groove may be a long and narrow indentation. Generally a groove can serve to allow another material or part to move within or along the groove and/or to be guided by the groove. Examples of grooves include, but are not limited to: a canal cut in a hard material, usually metal. The canal can be round, oval or an arc in order to receive another component such as a boss, a tongue or a gasket. The canal can also be on the circumference of a dowel, a bolt, an axle or on the outside or inside of a tube or pipe etc. This canal may receive a circlip, an O-ring, or a gasket; a depression on the entire circumference of a cast or machined wheel, a pulley or sheave. The depression may receive a cable, a rope or a belt; A longitudinal channel formed in a hot rolled rail profile such as a grooved rail. This groove may receive a flange of a train wheel. (Search "groove" on Wikipedia.com May 5, 2022. CC-BY-SA 3.0 Modified. Accessed Jun. 10, 2022.)

The groove 802 may include a contact surface 804 that engages the guide feature 190 as the guide feature 190 guides the hook into the opening (e.g., opening 702) of a bone. "Contact surface" refers to a surface or other feature of an object, instrument, or apparatus that is configured, designed, engineered, positioned, or oriented to contact another object, structure, or surface. In one aspect, a contact surface may be specifically configured for the contact with the other object, structure, or surface. For example, the contact surface may include a structure, cross-sectional shape, a contour, a contour shape, a feature, or a coating designed for the contact. For example in one embodiment, the contact surface may include a contour shape designed to facilitate and/or enhance contact and/or engagement between the contact surface and the other object. In another example, in one embodiment, the contact surface may include a lubricant to facilitate a sliding engagement between the contact surface and another object. Alternatively, the contact surface may include an adhesive to prevent or mitigate separation between the contact surface and another object.

The contact surface 804 may be configured in a variety of different configurations. In one embodiment, the contact surface 804 includes a contour shape. "Contour shape" refers to the shape of a contour that defines a surface such as a contact surface. In one aspect, a contour shape is a shape of a cross section taken perpendicular to a longitudinal axis of an elongated object. The contour shape can have a variety of shapes in one or more embodiments. For example, the contour shape can have a planar shape, a curve shape, an open polygon shape, a closed circular shape, and/or a closed polygon shape. "Curve shape" refers to a shape that is curved, circular, in the shape of a circle, oval, parabola, or ellipse, semicircular in shape, of a uniform circular shape, of a nonuniform circular shape, a half circle shape, a partial cannula, a half cannula, or the like. "Open polygon shape" refers to a shape formed by two or more line segments that join at one or more nodes and do not completely connect to form a closed polygon.

Figure 8C:
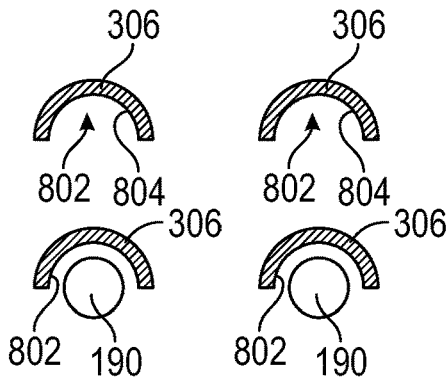

FIG. 8C illustrates the contact surface 804 of the groove 802 in example alignment feature 306. FIG. 8C also illustrates the contact surface 804 in contact with the guide features 190. In FIG. 8C the contact surface 804 may have a curve shape, for example a semi-circle contour shape. A curve shape for the groove 802 can facilitate removal of the hook plate 280 from the guide features 190, if needed. For example, the hook plate 280 can be simply placed on a superior side of the guide features 190, where the guide features 190 are K-wires. The curve shaped groove 802 enables engagement of the hook plate 280 and the guide features 190 without threading the alignment feature 306 (e.g., fully cannulated as in FIG. 8A) through the guide features 190. Alignment features 306 such as those of FIG. 8C can enable a surgeon to readily change the hook plate 280 as needed.

Figure 8D:
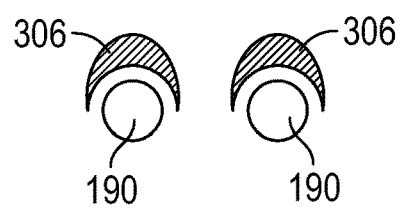
Figure 8E:
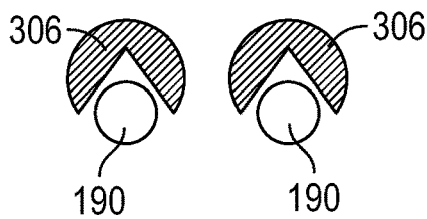
Figure 8F:
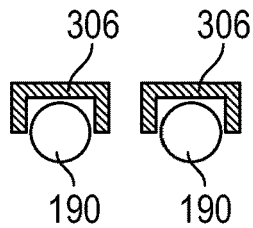

Those of skill in the art will appreciate that a variety of curve and/or open polygon shapes can be used for the groove 802. For example, the contour shape may be partial moon shape groove, a semi-circular shape groove, a polygon shape groove, and the like. FIG. 8D illustrates grooves 802 having a circular contour shape. FIG. 8E illustrates grooves 802 having an angled contour shape. FIG. 8F illustrates grooves 802 having an angled contour shape and an angled permitter, viewed in cross-section.

In certain embodiments, the groove 802 may not extend around a majority of the guide feature's surface. For example, the alignment feature 306 may include one or more rails 806.

As used herein, a "rail" refers to a structure that is longer than the structure is wide. A rail may be made from a variety of materials including, but not limited to, metal, plastic, ceramic, wood, fiberglass, acrylic, carbon, biocompatible materials, biodegradable materials or the like. Often a rail is made from plastic due to its lower expense, strength and durability. A rail may also be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. A rail may be coupled to another component or integrated with and/or form part of another component or structure. In certain embodiments, a rail may be configured or arranged to support another structure that may translate along, slide along, or otherwise move in relation to the rail. In certain embodiments, one rail may have a corresponding opposite rail such that the two rails for a pair of rails. The pair of rails may cooperate to support another component or structure as that structures moves in relation to the pair of rails.

Figure 8G:
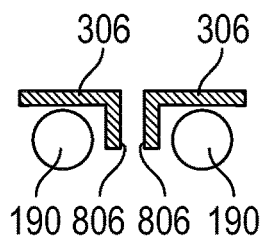
Figure 8H:
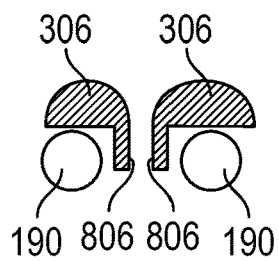

FIG. 8G illustrates an example embodiment in which the alignment feature 306 includes at least one rail 806. The rail 806 may extend along one side, or the other side, or both sides of the guide feature 190. In another embodiment, the rail 806 may extend from a body 282 of the hook plate 280. FIG. 8H illustrates an example alternative embodiment in which the alignment feature 306 includes at least one rail 806. Referring back to FIG. 8F, two rails 806 may together form a channel that accepts the guide feature 190.

Figure 8I:
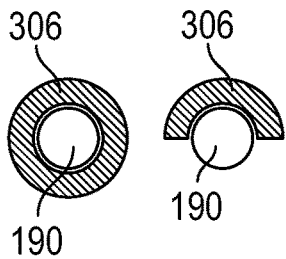
Figure 8J:
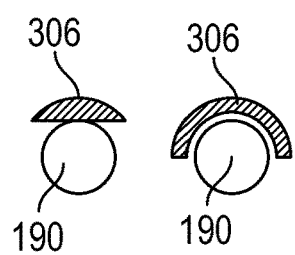

Of course the various combinations illustrated can be combined in various embodiments to facilitate use of the hook plate. FIGS. 8I and 8J illustrate two examples of combinations that may be used in various embodiments. Note in FIG. 8J that the contact surface 804 may include a planar shape.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects can exist alone and/or in a combination of fewer than all, or all, features of any single embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

It should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects can be present in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Those of skill in the art will appreciate that the solutions provided in present disclosure may be accomplished with all, or less than all, of the components, structures, features, or aspects disclosed in the specification or illustrated in the figures in relation or a particular embodiment or claim.

What is claimed is:

1. An implant configured to retain a bone of a patient, the implant comprising:
    a body extending between a proximal end and a distal end; and
    a hook comprising:
        a base extending proximal to the proximal end;
        a bend; and
        a prong extending from the bend, the prong slidably engaging a guide feature configured to guide the hook into an opening in the bone, wherein the prong remains engaged with the guide feature in a coaxial relationship as the hook is guided into the opening in the bone along the guide feature, and wherein a distal end of the prong is blunt.

2. The implant of claim 1, wherein the prong comprises an alignment feature configured to slidably engage the guide feature.

3. The implant of claim 2, wherein the alignment feature comprises a cannula comprising:
    a first opening near the prong;
    a second opening opposite the first opening, the second opening proximal to the bend; and
    a first diameter greater than a second diameter of the guide feature.

4. The implant of claim 2, wherein the alignment feature comprises:
    a groove that extends along at least a portion of the hook, the groove comprising a contact surface that engages the guide feature as the guide feature guides the hook into the opening in the bone; and
    wherein the contact surface comprises a contour shape selected from the group consisting of a curve shape and an open polygon shape.

5. The implant of claim 2, wherein the alignment feature comprises at least one rail that extends from the hook, the rail comprising a contact surface that slides along the guide feature as the guide feature guides the hook into the opening in the bone.

6. The implant of claim 2, wherein:
    the hook extends from the proximal end and wraps around at least a portion of an end of the bone; and
    the alignment feature is proximal to the prong of the hook.

7. The implant of claim 6, wherein the alignment feature slides linearly along the guide feature and seats wholly within the opening in the bone.

8. The implant of claim 1, further comprising a second hook extending proximal to the proximal end, the second hook configured to extend parallel to and aligned with the hook, wherein the second hook comprises a second alignment feature configured to engage a second guide feature to guide the second hook into a second opening in the bone.

9. The implant of claim 8, wherein the hook and the second hook define an open space between them sized to accept a bone fastener inserted into the bone, the bone fastener comprising a head having a diameter greater than the open space.

10. The implant of claim 1, wherein the guide feature guides the hook into the opening such that the bend contacts the bone proximal to the opening.

11. A hook plate system comprising:
    at least two guide wires configured to extend through a bone fragment, across a bone fracture, and into a parent bone of the bone fragment;
    a hook plate comprising:
        a body extending between a proximal end and a distal end;
        at least two cannulated hooks proximal to the proximal end of the hook plate, the at least two cannulated hooks extending parallel to each other and toward the distal end of the hook plate; and
        a plurality of fastener openings configured to accept a plurality of fasteners;
        wherein each of the at least two cannulated hooks comprises a cannula configured to slide along one of the at least two guide wires and at least partially into an opening in at least the bone fragment, the opening circumscribing the one of the at least two guide wires;
    a placement guide comprising:
        a placement guide body;
        a bone plate template that extends from the placement guide body, the bone plate template comprising a fastener template configured to identify locations for the plurality of fasteners of the hook plate; and
        two insertion guides that orient the at least two guide wires transverse to the fastener template as the at least two guide wires are configured to be inserted into and engage the bone fragment; and
    an inserter comprising:
        a coupler configured to releasably engage the hook plate; and
        an inserter body that extends proximally from the hook plate engaged by the coupler.

12. The hook plate system of claim 11, wherein the bone plate template of the placement guide comprises an inferior surface configured to match at least a portion of an inferior surface of the hook plate.

13. The hook plate system of claim 11, wherein the fastener template comprises a stop configured to interfere with insertion of at least one of the plurality of fasteners into the fastener template.

14. The hook plate system of claim 11, wherein the placement guide comprises at least a portion of an inferior surface configured to sit proximal to a distal end of the bone fragment without interference from one or more hooks of the hook plate.

15. The hook plate system of claim 11, wherein the two insertion guides comprise two openings that extend from one side of the placement guide body to an opposite side of the placement guide body, and wherein the two openings are parallel to each other.

16. The hook plate system of claim 11, wherein the placement guide comprises an engagement feature proximal to the two insertion guides, the engagement feature configured to engage a surface of the bone fragment.

17. A method for deploying a hook plate in a bone fragment at an end of a bone of a patient, the method comprising:

positioning a placement guide at an end of bone fragment reduced to a parent bone of a patient, the placement guide comprising:
  a handle;
  a bone plate template that extends distally from the handle;
  two insertion guides each comprising an opening configured to orient and guide a K-wire;
deploying two K-wires into the bone fragment and into the parent bone by way of the two insertion guides;
disengaging the placement guide from the two K-wires;
drilling a first opening that circumscribes one of the two K-wires and a second opening that circumscribes the other one of the two K-wires using a cannulated drill bit;
coupling two hooks of the hook plate with the two K-wires by way of alignment features of the hooks;
sliding the hook plate along the two K-wires by way of the hooks such that the hooks move at least partially into the first opening and the second opening; and
fixating the hook plate to the parent bone by deploying a fastener that engages the parent bone and the hook plate.

18. The method of claim 17, wherein sliding the hook plate along the two K-wires further comprises sliding the hook plate toward the parent bone by way of an inserter coupled to the hook plate and the method further comprises disengaging the hook plate from the inserter and wherein the first opening and the second opening each have a diameter greater than an outer diameter of each of the hooks of the hook plate.

19. The method of claim 17, wherein the first opening and the second opening each extend into bone of the patient for a first distance greater than a second distance between a distal end of each of the hooks and an apex of the hooks.

20. A hook plate system comprising:
at least two guide wires configured to extend through a bone fragment, across a bone fracture, and into a parent bone of the bone fragment;
a hook plate comprising:
  a body extending between a proximal end and a distal end;
  at least two cannulated hooks proximal to the proximal end of the hook plate, the at least two cannulated hooks comprising prongs extending parallel to each other and toward the distal end of the hook plate; and
  a plurality of fastener openings configured to accept a plurality of fasteners;
  wherein each of the prongs of the at least two cannulated hooks comprises a cannula configured to slide along one of the at least two guide wires and at least partially into an opening in at least the bone fragment, the opening circumscribing the one of the at least two guide wires;
a placement guide comprising:
  a placement guide body;
  a bone plate template that extends from the placement guide body, the bone plate template comprising a fastener template configured to identify locations for the plurality of fasteners of the hook plate; and
  an insertion guide that orients the at least two guide wires as the at least two guide wires are configured to be inserted into and engage the bone fragment, wherein the prongs of the hook plate are configured to be insertable into the bone fragment along the at least two guide wires engaged with the bone fragment; and
an inserter comprising:
  a coupler configured to releasably engage the hook plate; and
  an inserter body that extends proximally from the hook plate engaged by the coupler.

21. The hook plate system of claim 20, wherein:
the insertion guide is configured to orient the at least two guide wires transverse to the fastener template as the at least two guide wires are inserted into and engage the bone fragment.

22. The hook plate system of claim 20, wherein:
the insertion guide comprises two insertion guides extending from one side of the placement guide body to an opposite side of the placement guide body, and wherein the two insertion guides are parallel to each other.

23. A hook plate system comprising:
a hook plate comprising:
  a body extending between a proximal end and a distal end;
  a first hook extending from the proximal end of the body, the first hook comprising:
    a first base extending proximal to the proximal end of the body;
    a first bend; and
    a first prong extending from the first bend, the first prong slidably engaging
  a first guide wire configured to guide the first hook into a first opening in a bone; and
  a second hook extending from the proximal end of the body, opposite the first hook, the second hook comprising:
    a second base extending proximal to the proximal end of the body, opposite the first base;
    a second bend opposite the first bend; and
    a second prong extending from the second bend, opposite the first prong, the second prong slidably engaging a second guide wire configured to guide the second hook into a second opening in the bone;
  wherein the body of the hook plate is configured to slide along a surface of the bone parallel to a first longitudinal axis of the first guide wire and a second longitudinal axis of the second guide wire, as the first hook is guided into the first opening in the bone along the first guide wire and the second hook is guided into the second opening in the bone along the second guide wire;
a placement guide comprising:
  a placement guide body;
  a bone plate template that extends from the placement guide body, the bone plate template comprising a fastener template configured to identity a location for a fastener of the hook plate; and
  two insertion guides that orient the first and second guide wires as the first and second guide wires are configured to be inserted into and engage a bone fragment; and
an inserter comprising:
  a coupler configured to releasably engage the hook plate; and
  an inserter body that extends proximally from the hook plate engaged by the coupler.

24. The hook plate system of claim 23, wherein:
the two insertion guides are configured to orient the first and second guide wires transverse to the fastener template as the first and second guide wires are inserted into and engage the bone fragment.

25. The hook plate system of claim 23, wherein:
the two insertion guides extend from one side of the placement guide body to an opposite side of the placement guide body, and wherein the two insertion guides are parallel to each other.

26. The hook plate system of claim 23, further comprising:
the first and second guide wires, wherein the first and second guide wires are configured to extend through the bone fragment, across a bone fracture, and into a parent bone of the bone fragment.

27. An implant configured to retain a bone of a patient, the implant comprising:
a body extending between a proximal end and a distal end; and
a hook comprising:
a base extending proximal to the proximal end;
a bend; and
a prong extending from the bend parallel to the body, the prong slidably engaging a guide feature configured to guide the hook into an opening in the bone.

28. The implant of claim 27, wherein the prong comprises an alignment feature configured to slidably engage the guide feature.

29. The implant of claim 28, wherein the alignment feature comprises a cylindrical shape having a circular cross-section.

30. The implant of claim 28, wherein the prong remains engaged with the guide feature in a coaxial relationship as the hook is guided into the opening in the bone along the guide feature.

31. An implant configured to retain a bone of a patient, the implant comprising:
a body extending between a proximal end and a distal end; and
a hook extending from the proximal end of the body, the hook comprising:
a base extending proximal to the proximal end;
a bend; and
a prong extending from the bend, the prong slidably engaging a guide feature configured to guide the hook into an opening in the bone, wherein the hook is shaped to wrap around at least a portion of a distal end of the bone.

32. The implant of claim 31, wherein the prong comprises an alignment feature configured to slidably engage the guide feature.

33. The implant of claim 32, wherein the alignment feature comprises a cylindrical shape having a circular cross-section.

34. The implant of claim 32, wherein the prong remains engaged with the guide feature in a coaxial relationship as the hook is guided into the opening in the bone along the guide feature.

* * * * *